United States Patent
Kegelman et al.

[11] Patent Number: 5,985,672
[45] Date of Patent: Nov. 16, 1999

[54] METHOD AND APPARATUS FOR PRE-TREATING SAMPLES IN AN AUTOMATIC CHEMICAL ANALYZER

[75] Inventors: Joseph Edward Kegelman, Wilmington; John Paul Mizzer; Edward Anthony Nuzzaci, both of Newark; Allan Tit-Shing Chow, Wilmington, all of Del.

[73] Assignee: Dade Behring Inc., Deerfield, Ill.

[21] Appl. No.: 09/009,015

[22] Filed: Jan. 20, 1998

Related U.S. Application Data

[62] Division of application No. 08/638,618, Apr. 26, 1996, abandoned.

[51] Int. Cl.⁶ .................................................. G01N 35/02
[52] U.S. Cl. ................. 436/50; 436/43; 436/48; 436/49; 436/174; 436/180; 422/64; 422/67
[58] Field of Search ................. 436/43, 47, 48, 436/49, 50, 55, 174, 180; 422/63, 64, 67

[56] References Cited

U.S. PATENT DOCUMENTS

| | | | |
|---|---|---|---|
| 4,459,265 | 7/1984 | Berglund | 422/64 |
| 4,595,562 | 6/1986 | Liston et al. | 422/65 |
| 4,699,766 | 10/1987 | Yamashita | 422/64 |
| 4,906,433 | 3/1990 | Minekane | 422/64 |
| 5,037,612 | 8/1991 | Takahashi et al. | 422/64 |
| 5,104,808 | 4/1992 | Laska et al. | 436/48 |
| 5,147,529 | 9/1992 | Lee et al. | 210/695 |
| 5,183,638 | 2/1993 | Wakatake | 422/64 |
| 5,192,505 | 3/1993 | Sakagami | 422/64 |
| 5,212,094 | 5/1993 | Ogawa | 436/47 |
| 5,244,633 | 9/1993 | Jakubowicz et al. | 422/64 |
| 5,320,966 | 6/1994 | Mitsumaki et al. | 436/47 |
| 5,352,612 | 10/1994 | Huber et al. | 436/47 |
| 5,380,487 | 1/1995 | Choperena et al. | 422/63 |
| 5,434,083 | 7/1995 | Mitsumaki et al. | 436/48 |

*Primary Examiner*—Long V. Le
*Attorney, Agent, or Firm*—Leland K Jordan

[57] ABSTRACT

A pre-processor for use in performing heterogeneous immunoassays on samples for analytes in the sample employing concentrically positioned incubating and processing carousels. A single transfer station permits reaction vessels containing sample and reagents to be moved between the carousels. The samples are separated, washed and mixed on the processing carousel and incubated on the incubating carousel thus speeding up processing throughput.

8 Claims, 3 Drawing Sheets

METHOD AND APPARATUS FOR PRE-TREATING SAMPLES IN AN AUTOMATIC CHEMICAL ANALYZER

This is a divisional application of U.S. Ser. No. 08/638,618, filed Apr. 26, 1996, now abandoned.

FIELD OF THE INVENTION

The present invention relates to a method and apparatus for processing liquid samples and, more particularly, for processing biological fluids such as urine, blood serum, plasma, cerebrospinal fluid and the like. In particular, the present invention provides a method and means to automatically process a sample through a sequence of process steps that are carried out during heterogeneous immunoassays.

BACKGROUND OF THE INVENTION

Fully automated diagnostic analyzers are commercially available to perform chemical assays and immunoassays of biological fluids such as urine, blood serum, plasma, cerebrospinal fluid and the like. Generally, reactions between an analyte in a patient sample and reagents used during the assay, result in generating some sort of signal that can be measured by the analyzer. From this signal the concentration of analyte in the patient sample may be calculated.

Heterogeneous immunoassays are popularly used because their versatility allows both large and small sized analytes to be measured. They require three basic steps: (1) binding analyte to a solid phase, (2) separating the unbound sample analyte from the bound solid phase, and (3) measuring the bound analyte. The physical separation step eliminates most interfering substances, thereby providing for a higher sensitivity. Heterogeneous assays include competitive immunoassays and sandwich immunoassays. Diagnostic analyzers generally employ various processing stations, where processing operations such as sample and reagent addition, separate, wash, and mix are performed to accommodate such assays.

In a competitive assay, an antibody to an antigen contained in a first reagent is typically attached to a derivatized magnetic particle, i.e., particles that are responsive to a magnetic field, to make up a solid phase. The second reagent, consisting of antigen attached to a tag and a patient sample are mixed with the solid phase in a test tube. In the absence of patient antigen, some 50% of the antigen-tag is bound to the antibody of the magnetic solid phase. In the presence of patient antigen, some of the antibodies are attached to patient antigen and are unavailable to the tag antigen. As a result increasing amounts of patient antigen leads to decreasing amount of tag antigen. Magnetic separation clusters the magnetic particles of solid phase with the bound tag into a pellet on the side of the tube. The free tag can then be removed by thorough washing and aspiration. Following separation and removal of free tag, another reagent is added so that the amount of bound tag can be measured.

In a typical sandwich immunoassay, multiple steps are used, i.e., an antibody to an antigen is attached to the magnetic particle in high concentration relative to the amount of patient antigen in a sample. Patient antigen is captured by the antibody on the magnetic particles and then the particles (with attached or captured patient antigen) are separated from interfering substances in the sample. A second reagent, containing a second antibody with an attached tag, is added. This second antibody attaches to the patient antigen, captured by the first antibody on the magnetic particle, and results in the formation of a sandwich so that the second antibody tag is held firmly by the antigen to the first antibody on the magnetic particle. At this point, a thorough washing and magnetic separation permit the determination of bound tag which is in proportion to the patient antigen, the excess tag of the second reagent having been removed by the washing action.

In both types of heterogeneous immunoassays, considerable resources and time are required to achieve a sufficiently high degree of washing so as to eliminate interfering constituents and prevent spurious assay results. The degree to which this is achieved in an automated analyzer is an important contributor to the sensitivity of the analyzer.

High throughput is a desirable feature of such analyzers. An important contributor to maintaining a high throughput is the ability to process a plurality of samples through a variety of the different heterogeneous assay process steps that are needed before the signal measurement step may be undertaken. These multiple process steps tend to limit throughput. In the design of new automatic analyzers, in particular those involving complex "sandwich" heterogeneous immunoassays, which often require many separate processing operations, the ability to be capable of detecting a wide variety of analytes yet occupy a minimum of physical space, is an important performance advantage. Generally, repetitive, uninterrupted operation enhances throughput since a number of vessels can be processed simultaneously.

Repetitive operation is particularly difficult to achieve in the case of heterogeneous "sandwich" immunoassays. This is a particularly difficult procedure even when performed manually. It is a particular problem when the automatic wash procedure is incorporated into an automatic analyzer which is capable of performing multiple types of immunoassays. This necessitates the use of multiple wash stations and this is typically accomplished in automatic analyzers by providing such multiple wash stations. For example, the sensitivity requirements of some heterogeneous assays demand that the washing efficiency must be very high. This is normally achieved by repeated washes, each successive wash removes unwanted liquids and reagents so that a progressively lower background level is achieved. At the same time, such a washing regimen places limitations on use of the various processing resources since the analyzer is required to be stationary in a washing activity. Nominally, an assay requires a total of four separate washes interlaced with four separation steps. Accordingly, an important design feature of the analyzer is the ability of non-washing resources to be productively involved with one sample while another is being washed. However, the several mechanisms required to operate individually the several wash stations and the mechanisms required for the wash stations themselves can become quite expensive.

U.S. Pat. No. 4,459,265 assigned to Clinicon describes an automatic analytical apparatus with a stepwise rotatable circular plate. It carries a plurality of reaction tubes on its periphery with several reagent supply stations arranged at different locations around such periphery. The use of multiple stations does provide the machine with the versatility to carry out several different test methodologies, but again does not provide the necessary washing required for heterogeneous immunoassays. The automatic analytical apparatus described in such Clinicon patent, includes a stepwise rotatable circular plate. It carries a plurality of reaction tubes on its periphery with several reagent supply stations arranged at different locations around such periphery. The use of multiple stations does provide the machine with the versatility to carry out several different pre-assay process steps, but again does not provide the necessary washing required for heterogeneous immunoassays.

A conventional chemical analyzer produced by Hitachi, Inc., Tokyo, Japan, Model Number 7050, links together or "gangs" plural wash probes. When this is accomplished, however, the ability of the instrument to perform multiple analytical procedures at the same time is impaired.

U.S. Pat. No. 5,104,808, Laska et al., assigned to the assignee of the present invention, also describes an analyzer which "gangs" wash probes together. The wash probes are ganged together, but also separated into two groups to achieve the goal of providing washed solid support which contains a minimal amount of the original serum/conjugate matrix. According to Laska et al. the wash means includes at least two wash probes coupled or ganged for simultaneous insertion into the reaction vessels at different processing positions. Further, the wash probes are positioned contiguous to the first one of the sample and/or reagent positions in the sequence. The means for adding sample and/or reagents is disabled each cycle for a number of vessels leading and trailing the first and last vessels receiving sample or reagent, the number corresponding to the number of processing positions between the insertable wash probes.

U.S. Pat. No. 5,183,638, Wakatake; discloses an analyzer in which a reaction vessel is conveyed past several devices for adding and agitating magnetic particles as required during a EIA immunoassay.

U.S. Pat. No. 5,192,505, Sakagami, discloses an analyzer in which two different reaction lines are provided, driven by only one driving device, one line adapted to provide for assay operations involved in a calorimetric measurement, the other line adapted to provide for assay operations involved in an immunization agglutination measurement. An advantage of the analyzer is maintenance of a small physical size.

Another feature used in automated analyzers is the scheduling method used to present the sample to the various assay tools. As described in U.S. Pat. No. 5,212,094, an automatic chemical analyzer uses an odd number of reaction vessels disposed in a circular pattern. The reaction vessels are rotated successively half revolutions of the circular pattern plus the distance between reaction tubes. Using such a pattern, it is possible to collectively situate the washing stations proximate one another and thereby facilitate compactness of the analyzer, however such an analyzer is not capable of performing heterogeneous immunoassays.

The analyzer of U.S. Pat. No. 5,352,612 includes a movable sample support for holding samples arranged in a first, plurality of positions for movement in a first direction. An indexing drive for the sample support moves the samples in the sample support in the first direction in a set of increments wherein each increment represents a movement of the samples an amount corresponding to a number of samples. Such a system enables separation of logical space from physical space in the system, allowing more freedom in placement of mechanical equipment while permitting proper sequencing of operations both in space and in time. This system requires a very complex time-indexing motion of a rotatable sample support that is determined differently for each and every loading of the sample support. As best understood, the movement pattern is determined by the number of pairs of reaction cuvettes. The pattern may vary depending on the assay to be performed and the times spent stopped before different processing resources varies according to the operation of the processing resource.

U.S. Pat. No. 5,380,487, assigned to Pasteur Sanofi Diagnostics, describes an analyzer in which assay resources are assigned fixed operating sequence which begin and end within a time cycle of fixed duration. When different samples having different assay protocols are entered into the analyzer, assay resource requirements for the different samples are determined and "time slots" of the required resources are allocated thereto. Provision is made for handling heterogeneous assays, however because an incubator belt physically intersects the wash wheel, a complex relationship is established between the indexing time of an incubator belt, the indexing time of a wash wheel, and the cycle time of operations performed on reaction vessels as they are moved along the wash wheel. In addition, the control means must determine which time-based assay resources are required to process a test and then check the availability of those assay resources on a cycle-by-cycle basis against the allocation of the resources to the processing of other tests underway. Absent any conflicts in the allocation of assay resources, processing of a reaction vessel will sequentially follow a preceding reaction vessel. Consequently, initiation of the sample processing for a test may be delayed until all the necessary assay resources are available for processing. Although such scheduling may reduce the overall number of indexing cycles necessary to complete the processing of all the tests, scheduling conflicts do delay processing initiation and also result in processing resources being idled.

From a study of the different approaches taken in the prior art to the problems encountered with automated processing of complex heterogeneous immunoassays, there is a need for improved automated analyzers and associated processes for handling samples. At the same time, there is a need for maintaining a high throughput without introducing complex programming and, at the same time, minimizing the physical size of an analyzer. In particular, there is a need for a method of providing bound-unbound analyte separation and wash in a minimum of processing time, in a pattern that enhances/ maintains throughput of an automated analyzer.

It is an object, therefore, of the present invention to provide an apparatus for providing the operations required in heterogeneous immunoassays at an increased efficiency and with greatly simplified sample handling techniques.

SUMMARY OF THE INVENTION

Many of these disadvantages of the prior art are overcome by using the apparatus and/or methods of this invention. This invention provides a method pre-processing samples having a solid support for heterogeneous assays, using a processing carousel and an incubating carousel, for detecting an analyte in said samples, comprising the steps of:

(a) adding tag reagents, including said solid support, to the sample on said incubating carousel, thereby forming a tagged sample analyte-support complex, (b) transferring the sample and reagents to the processing carousel, (c) separating the solid support from at least a portion of the sample and reagents, (d) washing the solid support, (e) mixing the solid support with a wash buffer, and (f) transferring the solid support and buffer to the incubation carousel, and (g) detecting the analyte.

The number and sequence of steps is selected so that each reaction vessel transferred onto the processing carousel may be removed from the processing carousel at the transfer station for additional processing and returned to the processing carousel using the single transfer station without interrupting the repeated synchronous pattern.

Such a novel approach makes it possible to achieve the rigorous requirements for washing samples required in heterogeneous immunoassays. This is true even though several tests or assays have different reaction times before a wash and may include a reagent addition and incubation step interlaced within the required wash cycles.

Associated with this method is an automatic sample processor for performing pre-immunoassay operations on samples using a solid support. The processor in an analyzer for detecting an analyte, in a sample, using solid supports, said processor comprising:

a processing carousel supporting a plurality of reaction vessels each adapted to hold a sample, an incubating carousel, supporting a plurality of reaction vessels each adapted to hold a sample, positioned concentrically of said processing carousel, stationary processing stations positioned adjacent one of said carousels, said stations having means for separating said solid support from the contents of a reaction vessel, means for washing the contents of a reaction vessel, and means for mixing the contents of a reaction vessel, drive means to rotate each carousel independently of the others, said processing carousel being driven in a repetitive manner to position each of its reaction vessels to positions contiguous predetermined processing stations, and transfer means for transferring reaction vessels between said carousels, thereby improving processing time by permitting the incubation of all reaction vessels on the incubating carousel without interrupting sample processing on the processing carousel.

The processing stations are positioned in a preselected order to permit the processing carousel to position its reaction vessels in a repetitive sequence of separation and the wash steps. More specifically, the reaction vessel repetitive sequence is separation, wash, and mix. These features provide an analyzer that has a high throughput, reduces the cost of the processing stations by locating similar functions together, and permits samples being processed to be removed at virtually anytime for incubation or measurement.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE PREFERRED EMBODIMENT

Figure 1:
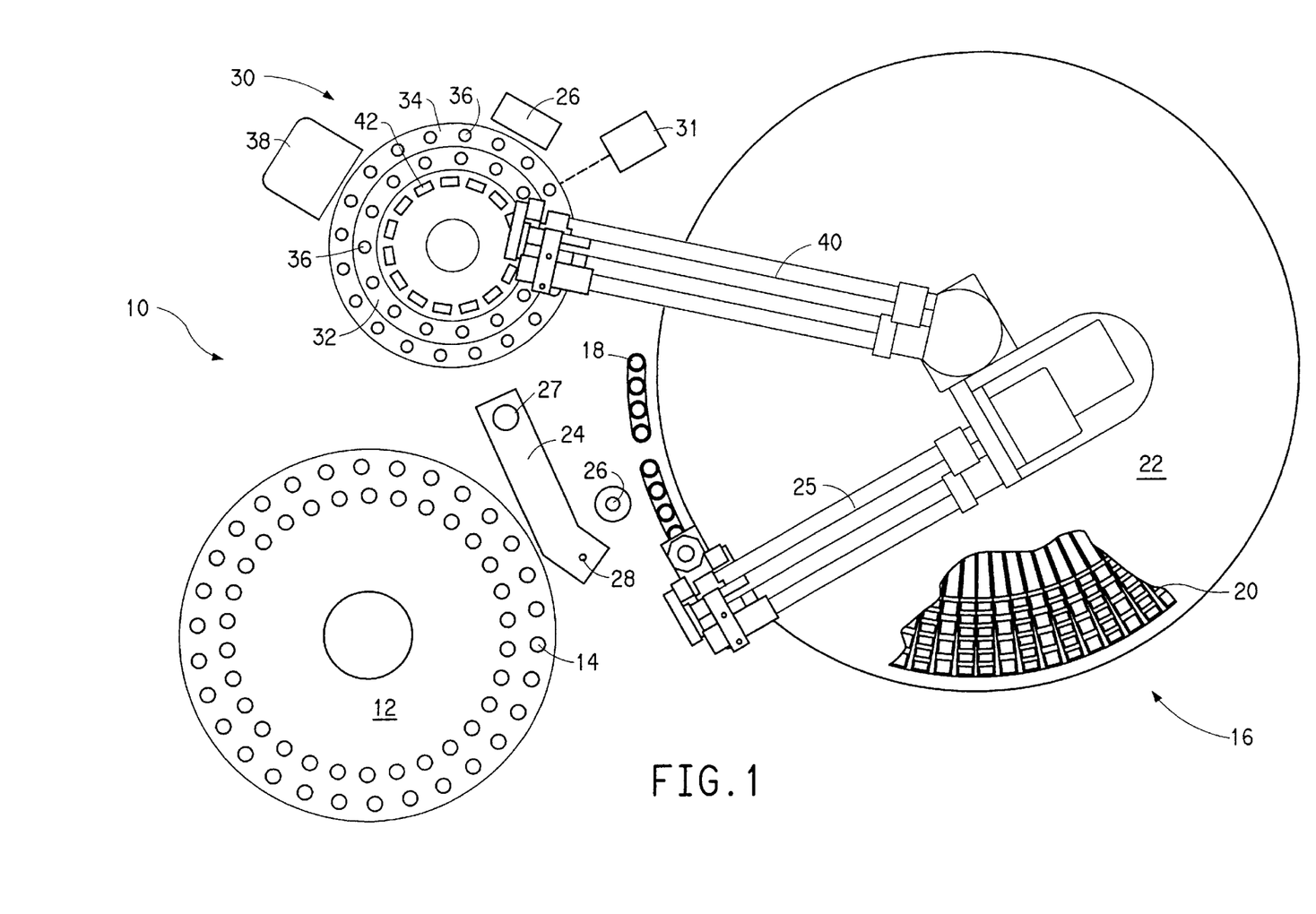
FIG. 1 is a schematic plan view of an automated chemical analyzer having a pre-assay processor with a movable processing carousel, an incubating carousel, and a plurality of processing stations for pre-assay processing of samples.

The method and apparatus of this invention will be described initially with particular reference to FIGS. 1 and 2 of the drawings. FIG. 1 shows schematically the elements of a conventional automatic chemical analyzer 10 comprising a sample cup carousel 12 supporting a plurality of sample cups 14, a cuvette carousel 16, adapted to hold a plurality of cuvettes 18 and to provide plurality of reagent liquid cartridges 20, illustrated as disposed beneath a cut out portion of a lid 22, which covers various thermally controlled areas. Reagent cartridges 20 are preferably a multi-compartmented container such as those sold under the tradename FLEX™ by E.I. du Pont de Nemours and Co., Inc., Wilmington, Del. Cuvettes 18 may be formed, as done on the Dimension® chemical analyzer sold by E.I. du Pont de Nemours and Co., Inc., Wilmington, Del. by pulling two different composition ribbons of clear film from a cuvette film cartridge, not shown, onto the periphery of the cuvette carousel 16. The cuvette carousel 16, preferably in the form of a wheel, has about a hundred separate cavities for holding cuvette 18, the inner wall of each cavity having an opening to allow transmission of light. A small opening remains at the top of each cuvette 18 to allow the addition of reagent liquid and sample liquid. A sample liquid arm 24 and a wash resource 26 are located proximate the sample cup carousel 12 and cuvette carousel 16. Sample liquid arm 24 supports a conventional sample liquid probe 28 and is mounted to a rotatable shaft 27 so that movement of sample liquid arm 24 describes an arc intersecting the sample cup carousel 12, the cuvettes 18, and the wash resource 26. The wash resource may be used to clean the probe 28.

A first liquid probe 25 is rotatably mounted above cuvette carousel 16 and is adapted to draw reagent liquid from an appropriate reagent liquid cartridge 20 and deposit each reagent liquid within a predetermined cuvette 18 for processing by the chemical analyzer 10. Probe 25 further comprises an ultrasonic mechanism used for aspirating, dispensing and mixing reagents similar to that used in the Dimension® chemical analyzer. Since the hydrating, aspirating, dispensing and mixing mechanisms are well known in the art they need not be described further. Photometic analyzing means, not shown, located beneath the cuvette carousel 16 measures light absorbence through the cuvettes 18 at various wavelengths, from which the presence of analyte in the sample liquid may be determined using well-known analytical techniques. Thus far, the chemical analyzer is conventional and may be, for example, the Dimension® clinical analyzer sold by E.I. du Pont de Nemours and Co., Wilmington, Del.

This invention adds to that analyzer a pre-assay sample processing module 30. This facilitates the several additional steps necessary to perform heterogeneous assays without reducing the ability of the chemical analyzer to maintain a high sample throughput. The processing module 30 permits processing either or both of the sample liquid with analyte and/or the reagent liquid, before they are provided to a cuvette 18 for measurement. Sample processing module 30 comprises two pre-assay sample treatment carousels 32 and 34. These are an inner processing carousel 32 and an outer incubation carousel 34, housed in a thermal chamber, (not shown), the two carousels being concentrically mounted with a common axis and preferably lying in a common plane, both preferably being in the form of a circular carousel. Both carousels are independently moveable and have a predetermined number of vessel holding means which may be clips, not shown, to support a plurality of individual pre-assay reaction vessels 36.

Drive means 31 are provided for independently rotating incubation carousel 34 and processing carousel 32 about a common axis, the drive means typically comprising gear teeth disposed on each of the carousels 32 and 34 and interlacing with pinion gears mounted on the shaft of a motor (not shown). The drive means may be of conventional design. The transfer station 38 described above is one of the plurality of processing stations.

The incubation carousel 34 preferably contains 45 discrete positions, and is situated to allow reaction vessels 36 to be presented for: 1) reagent addition, 2) sample addition/ aspiration, and 3) transfer to/from the cuvette and processing carousels 16, 32, and for load/unload. The carousel may be about 10 inches in diameter. The incubation carousel 34 is driven via a drive means 31 and uses a single home sensor. Its position can be verified at any time via an encoder attached to the stepper motor.

The incubation carousel 34 is slotted to allow vessels to be transferred on/off the carousel horizontally.

When vessels 36 are on the incubation carousel 34, they move inside a thermal incubation trough, which guides the vessels as they travel around the carousel, and keeps them at a steady temperature. The incubation trough is aluminum and heated via a resistive element. A thermistor senses the metal temperature nearest the vessels.

The incubation carousel operation is asynchronous; i.e., it can position any of 45 vessels to any of three locations as noted above at any time. This provides flexiblity in assay formats and complete random access.

The processing carousel 32 contains 15 discrete positions, and is situated concentric inside the incubation carousel. The processing carousel allows the vessels to be presented for: 1) magnetic separation, 2) aspirate/wash, 3) re-suspension mixing, and 4) transfer on/off the processing carousel to the incubation carousel. The processing carousel 32 may be about 7 inches in diameter.

The processing carousel 32 is driven by the drive means 31, by the same as the incubation carousel. Similar to the incubation carousel, the processing carousel is slotted to allow vessels to be transferred on/off. The vessels are held in place on the carousel with spring clips.

Unlike the incubation carousel, the sequencing of the processing carousel is synchronous or repetitive. Whenever reaction vessels 36 are present on the carousel, the carousel will index in a rote manner, advancing each vessel through a series of separate-wash-mix steps.

Generally, repetitive operation enhances throughput, but places certain restrictions on assay formats and random access capability. Since 15 reaction vessels can occupy the carousel and process simultaneously, throughput is enhanced. However, since the processing carousel operates independent of the incubation carousel, flexible assay formats and complete random access processing is still achieved.

The sensitivity requirements of some heterogeneous assays demand that the processing station efficiency must be very high. This invention permits repeated washes of each reaction vessel, in order to ensure the desired near-zero background levels. Nominally, each assay has a total of 4 separate/wash sequences.

A common transfer station 38, which accesses both carousels 32 and 34, is provided for transferring reaction vessels 36 between the two carousels 32 and 34 and for removing reaction vessels 36 from the sample processing module 30 and passing them into a suitable waste disposal, not shown.

The transfer station 38 (FIG. 2), which may be of conventional design, is used to transfer reaction vessels 36 to/from the processing carousel and to load/unload vessels from the incubation carousel 34. All vessel transfers are done in the horizontal plane only, by simply sliding the vessels along their path on a slider 39. The slider 39 is driven via a stepper motor, (not shown), and can locate the vessels anywhere along the transfer station 38, i.e., over either of carousels 32 or 34. An encoder is used to verify positioning of the slider. As the design must allow for new vessels to come in and old ones to clear, a 'T' track 46 is employed. A solenoid driven gate (not shown) is closed to allow new vessels to be loaded.

New vessels are routed to the vessel transfer station 38 via the feedtrack 44. A drive wheel 48, located at the end of the feedtrack 44 near the transfer station, is used to provide positive drive of a stack of vessels (not shown) when the system is loading a new vessel into position for transfer onto the incubation carousel 34.

Used vessels are routed to the waste container via a plastic chute 41 attached to the underside of the transfer station, beneath a hole in the exit track (not shown).

A second liquid probe 40 is rotatably mounted above cuvette carousel 16 and is adapted to draw reagent liquid from an appropriate reagent liquid cartridge 20 and deposit such reagent liquid in a predetermined reaction vessel 36 in the incubation carousel 34. Sample liquid probe 28 is also adapted (1) to draw sample liquid from a reaction vessel 36 after the sample liquid has undergone the scheduled pre-assay operations and (2) to deposit sample liquid within a predetermined cuvette 18 for further processing and measurement.

In accordance with this invention, sample processing devicps, or stations 42 (FIG. 1), are positioned at selected circumferential locations about the processing carousel 32 such that they can access reaction vessels 36. It will be recalled the processing carousel 32 is concentrically mounted with the incubating carousel 34, radially outside of the processing carousel 32 (depicted in FIG. 1 as inside for the sake of clarity).

These stations are adapted to provide for mixing together of the sample liquid and the reagent liquid contained in a reaction vessel 36, for washing the sample liquid and the reagent liquid contained in a reaction vessel 36, and for magnetic separation of tagged magnetic particles from free tags or reagent liquid contained in a pre-assay reaction vessel 36.

Two wash stations W1 and W2 (FIG. 2) are used to aspirate away unbound sample and/or reagent from reaction vessels, and possibly replenish the vessel with a wash buffer for subsequent steps.

The wash station module comprises a casting that holds two dual wash probes (W1 & W2), allowing two vessels to be washed concurrently. The probes are spring loaded, which ensures reliable contact with the bottom of each vessel for complete aspiration. The probes operate on adjacent vessels; if only one vessel is present, only one probe is aspirated/dispensed. The probes are positioned up/down via a stepper motor. The position is verified using a home sensor after each operation.

Figure 2:
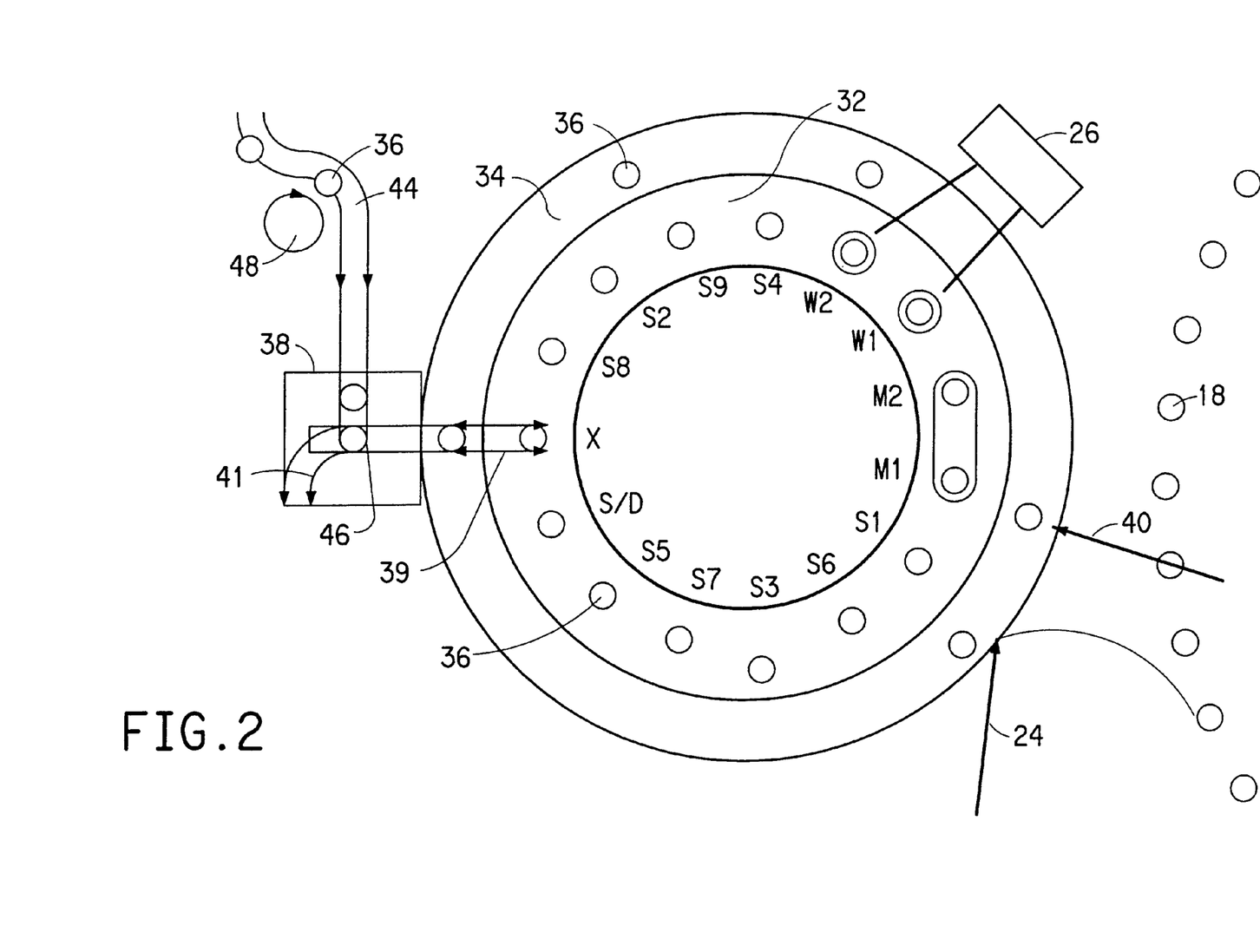
FIG. 2 is a schematic plan view of the pre-assay processor of FIG. 1.

There are two mix stations M1 and M2 (FIG. 2). They are used to re-suspend the separated magnetic particles in the wash buffer after each wash. The mixer employs a vortex external mixer design, which avoids any contamination with the sample/reagents while mixing. Mixing station M preferably impart a vortexing mixing action to reaction vessels 36 as is a usual practice in the manipulation of samples in chemical laboratories. Devices are available for this purpose and preferably comprise an externally mounted disc which is placed against the bottom of the reaction vessels and eccentrically rotated.

Design of the mix station is conventional, for example, as described in U.S. Pat. No. 4,848,917, Benin et al. assigned to the assignee of the present invention. In a preferred embodiment, external contact is made with the vessel(s) using a mixing pad to engage the vessel bottom tips. The vessel is then wobbled in an eccentric motion, causing the vortex mix. The mixing pad is normally recessed about 0.050 inches below the vessel bottoms, so that the vessel tips will clear while the wash carousel is advancing them between stations. When vessels are in position for a mix, the mixing pad is elevated to make contact with the vessels. The elevation is achieved via swing-out cams, which engage when the mix motor is energized and reaches a certain speed. A sensor is used to detect that the mix pad is properly engaged.

As with the wash stations, the mix stations M1 and M2 can operate on two vessels concurrently. Normally, two adjacent vessels are mixed simultaneously; however, the mixer is capable of mixing either of the two adjacent vessels if the other one is missing.

The separation stations S1 to S9 (FIG. 2) as conventional and typically include magnets positioned adjacent the locations of the reaction vessels 36 for attracting the magnetic solid support particles (such as those described in U.S. Pat. No. 5,104,808) to the walls of the reaction vessel such that unbound material may be aspirated.

FIG. 2, as noted, shows various stationary processing stations (described above) disposed contiguous the processing carousel 32. The drive means 31 for controlling movement of carousels 32 and 34 is conventionally controlled by a controlling unit, preferably a microprocessor based central processing unit (CPU), housed in the analyzer 10 to move the vessels index-stepwise to each processing station 42 where at pre-assay processing occurs, as described below. The control is provided by software, typically like that used on the Dimension® clinical chemistry analyzer and is widely used by those skilled in the art of computer-based electromechanical control programming. The rotating means are preferably commercially available stepper motor mechanisms.

In accordance with the present invention, the processing carousel 32 is indexed to successive processing locations or stations 42 capable of performing various pre-assay operation. The samples at each station are subjected to various pre-assay operations for a constant time period. FIG. 2 shows the processing carousel 32 preferably associated with pre-assay treatment stations distributed as follows: ten separation stations (S1 . . . S10), two wash stations (W1, W2), and two mix stations (M1, M2), and the transfer station 38.

The important time-templating features of the processing carousel 32 of the present invention are described next in detail. These are implemented by operating software programs which will be described in conjunction with the FIG. 3. It has been discovered that if a particular relationship is established between the number and location of processing stations on processing carousel 32 and the sequence at which reaction vessels 36 are repetitively indexed to processing stations 42 is maintained, then it is possible to significantly increase the efficiency of pre-assay processing of samples undergoing heterogeneous assays. These samples may require either a first reagent addition, sample-support separation, sample mix and sample wash and/or a second reagent addition, a second sample-support separation, a second sample mix and a second sample wash.

In order to achieve the pre-assay protocols associated with these alternate pre-assay requirements, it has been discovered that one can use repetitive sequences or patterns of movement for each of the reaction vessels 36 to the several processing stations 42, i.e., S, W, and M.

Figure 3:
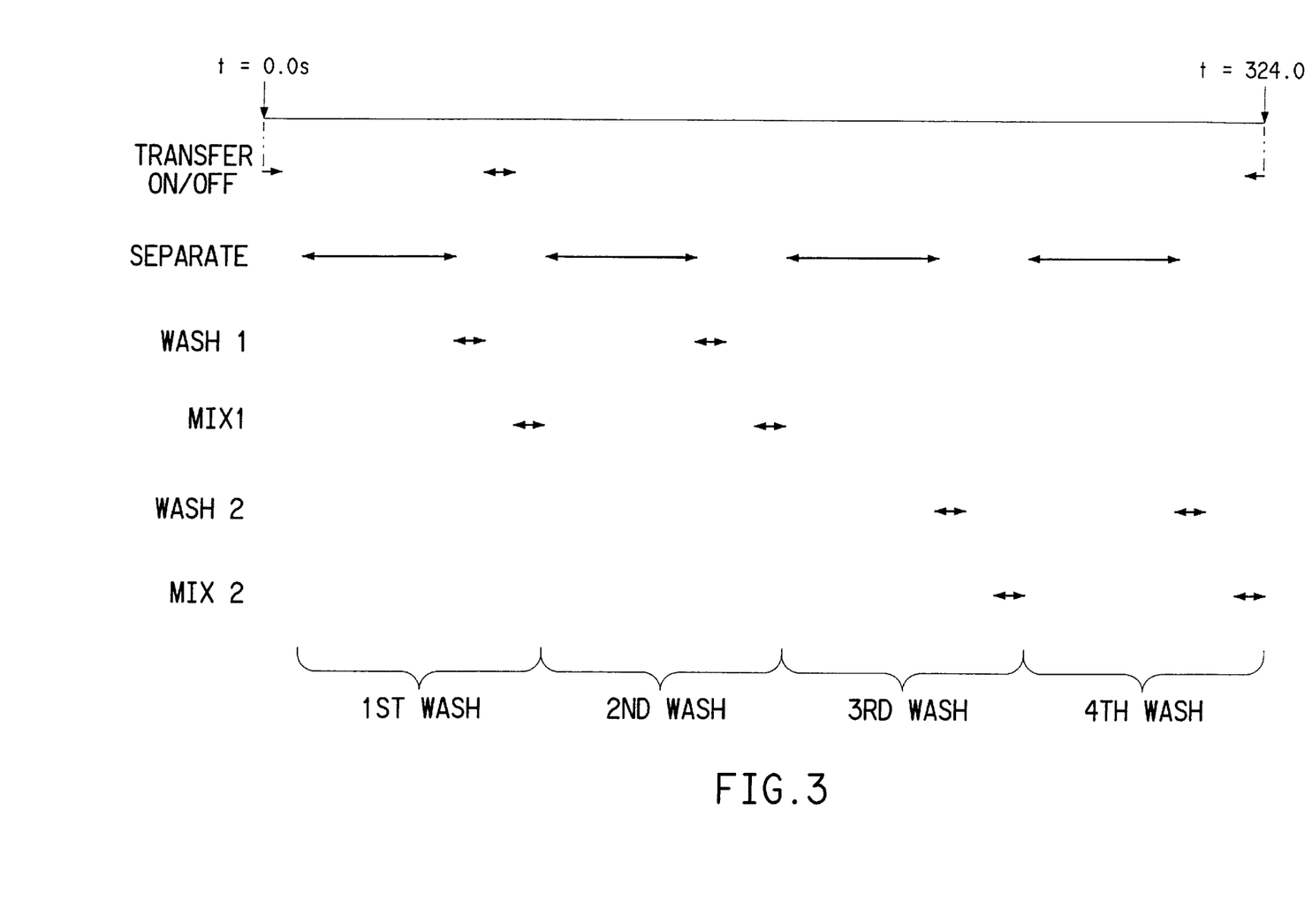
FIG. 3 is a timing diagram for the pre-assay processor.

In accordance with this invention, rather than index or sequence the processing carousel 32 one position at a time, a novel technique is used to advance the vessels unique segments or groups of index positions at a time. The processing carousel 32 has 15 stations, hence there are 15 indexes or positions to index the carousel for a complete revolution. The advancing is always in the same direction and alternates between incrementing groups of +6 indexes or positions and +7 indexes or positions of the processing wheel (FIGS. 2 and 3). Applying this sequence to the processing carousel 32, it can be seen that a reaction vessel 36 entering at "X", the transfer station, and advancing a total of 30 groups of indexes, would transition through all the stations in this pattern:

TABLE 1

| | |
|---|---|
| X-S-S-S-S-S-W1-X-M1 | (first wash) |
| -S-S-S-S-W1-S-M1 | (second wash) |
| -S-S-S-S-W2-S-M2 | (third wash) |
| -S-S-S-S-W2-S-M2-X | (fourth wash) |

This sequence provides the needed four separate/wash/remix steps using 30 groups of indexes. Simultaneous assays would use all four washes consecutively. Sequential assays would use the 1st separation/wash steps after the first incubation, and the 2nd, 3rd, and 4th separation/wash steps after the second incubation.

As depeicated in Table 1, above, starting from the point of entry at the transfer station, each and every reaction vessel 36 in processing carousel 32 undergoes a first indexing segment or STEP 1 in which the processing carousel 32 is indexed counter-clockwise past five intervening processing stations without stopping to the sixth-next processing station S1. Thus, a first reaction vessel at station X is transferred counter-clockwise by a synchronous movement of the inner carousel 32, past five intervening processing stations to the seventh processing station S1. After the same constant predetermined time of operation, the processing carousel 32 is indexed repetitively counter-clockwise past six intervening processing stations without stopping, to the seventh-next processing station S2. This repetitive pattern of movement of indexing forward first to the sixth-next processing station, followed by sample treatment for a constant predetermined time of operation, and then indexing forward to the seventh-next processing station is repeated with the indexing always in the same direction, forward or counter-clockwise as seen from above, without stopping regardless of the assay to be performed. A reaction vessel 36 on processing carousel 32 thereby experiences a first rotational movement which comprises six carousel step-indexed movements "forward", each indexed segment movement followed by a stopped time at the aligned processing station Mn, Sn, or Wn as indicated for a constant time amount of pre-assay sample treatment. This repetitive pattern of six-seven index segments is repeated as explained below when needed to perform five separate treatments, i.e., single wash and single mix pre-assay processing treatments as in the instance of a "single-reagent" heterogeneous assay. In the instance of a so-called "two-reagent" heterogeneous assay, the reaction vessel 36 may be removed from the processing carousel 32 for additional reagent treatment, as explained below and then re-placed on the processing carousel 32.

Applying this sequence to the processing carousel 32 arrangement as shown in FIG. 2, it can be seen that a vessel entering processing carousel 32 from the transfer station 38, and indexing a total of 30 index segments would make two complete revolutions around the carousel, and would transition through all the required stations before being presented to the transfer station 38 for transfer to the incubation carousel 34 where sample aspiration may occur. This sequence provides four separate wash cycles of separate, wash, and mix cycles using 30 index segments. In the case of a sequential assay, after the first wash cycle is completed, the reaction vessel is located at the transfer station. Certain sequential assays require an additional reagent addition and incubation period after the initial transfer to incubation carousel 34 and thereafter are transferred back onto processing carousel 32 to complete the separation process, again processing through the second, third and fourth wash cycles as needed.

This increased throughput is made possible by using a repetitive movement of the processing carousel 32, in which each of the reaction vessels 36 on the processing carousel 32 are presented to processing stations Sn, Mn and Wn in an ordered manner, each vessel 36 being processed by the station where it is moved during the synchronous movement of the processing carousel 32, each vessel furthermore being processed by the different devices Sn, Mn, and Wn for a same constant amount of time.

The timing sequence for these wash cycles is shown in FIG. 3 and the timing sequences is calculated by the CPU of the analyzer 10. Without regard to the express times at the several processing stations 42, the repetitive sequence making up the several wash cycles may be better understood with reference to Table 2. The appropriate choice of the number of processing stations and devices, in combination with assigning to each processing station a same constant amount of processing time regardless of the capability of the station enables the throughput of processing carousel 32 to exceed normal expectations.

Furthermore, in accordance with the present invention, is the ability to handle a plurality of reaction vessels, up to a maximum of fourteen, and present each one of the reaction vessels to the required resource in the required order, the number of resource stations being equal to fifteen stations.

TABLE 2

| | First Wash Cycle | | | | | | | |
|---|---|---|---|---|---|---|---|---|
| Step | 1 | 2 | 3 | 4 | 5 | 6 | 7 | 8 |
| Processing Positions | +6 | +7 | +6 | +7 | +6 | +7 | +6 | +7 |
| Stations 42 | S1 | S2 | S3 | S4 | S5 | W1 | X | M1 |
| | Second Wash Cycle | | | | | | | |
| Step | 9 | 10 | 11 | 12 | 13 | 14 | 15 | |
| Processing Positions | +6 | +7 | +6 | +7 | +6 | +7 | +6 | |
| Station 42 | S2 | S6 | S4 | S7 | W1 | S/D | M1 | |
| | Third Wash Cycle | | | | | | | |
| Step | 16 | 17 | 18 | 19 | 20 | 21 | 22 | |
| Processing Positions | +7 | +6 | +7 | +6 | +7 | +6 | +7 | |
| Station 42 | S8 | S6 | S9 | S7 | W2 | S/D | M2 | |
| | Fourth Wash Cycle | | | | | | | |
| Step | 23 | 24 | 25 | 26 | 27 | 28 | 29 | 30 |
| Processing Positions | +6 | +7 | +6 | +7 | +6 | +7 | +6 | +7 |
| Station 42 | S8 | S1 | S9 | S3 | W2 | S5 | M2 | X |

A "dummy station" D is located as shown at the first counter-clockwise location next adjacent the transfer station 38. It is labeled S/D because it has a separation magnet to maintain any magnetic particles in reaction vessels 36 at that station clustered. The presence of and positioning of "dummy station" D enables the use of a repetitive pattern chosen to present each one of the reaction vessels 36 to the required processing station in the required order. As a result of the particular distribution of pre-assay processing stations in a circular pattern, coupled with the particular movement pattern being broken into four cycles, each reaction vessel is sequentially positioned at sub-groups of separate, wash, mix, stations, allowing the ancillary devices (motors, stirring pads, drains, etc.) that support the action of the two wash probes and the mixers to be ganged together for a compact design.

This technique provides:
  reduced carryover potential, as the W1 wash station is used for first 2 washes, and the W2 station for final 2 washes,
  the wash stations and mixers are located adjacent one another, allowing the 2 wash probes and mixers to be ganged together for a compact design,
  increased throughput when processing sequential assay formats that require a 1st phase sample wash and a 2nd phase reagent wash.

In addition to achieving the desired result of positioning like processing stations proximate one another, so as to achieve maximum utilization of supporting devices (motors, pumps, common stirring pad, drains, etc.), once the processing carousel 32 is totally full of reaction vessels 36, for example, as would occur during high volume processing, all vessels are being actively used in either a separate or mix station, except for those vessels positioned at either a X or D position. As many as 13 other reaction vessels 36 may be at different stages in the pre-assay treatment positions afforded by the processing carousel 32 and still allow for an additional reaction vessel to be entered onto the carousel, requiring only that the transfer station X be vacant.

The present invention uses a novel positioning and advancement of the reaction vessels 36 to provide increased throughput when processing heterogeneous sequential assay formats which require an initial wash cycle followed by a reagent addition to accomplish tagging of the antibody and then a final wash cycle. A surprising result of this apparatus is the ability to accomplish high throughput for competitive assay formats which require a first and second incubation. Throughput is a function of the assay requirements, the available resources to service these requirements, and how well the resources are scheduled. All of these must be balanced. It has been found that the present invention provides a proper balance of all of these essential elements to provide an optimum throughput, regardless of whether the assay is simultaneous or sequential.

When fully loaded with a maximum of 15 reaction vessels 36, all vessels may be sequentially stepped through the required stages of separation, wash, and mix in an almost continuous fashion without interrupting the sequential stepping motion of processing carousel 32. This feature has been found to provide a significant reduction in processing time over that which would have been required if the pre-assay steps were handled in the more conventional pattern of completing each reaction vessel's 36n pre-assay processing before starting another and/or of ganging together a small number of reaction vessels for pre-assay treatment.

In a particular embodiment, the pre-assay processing carousel 32 of the present invention is designed and depicted in FIG. 3 to process heterogeneous assays using an index time for each step of the processing carousel 32 of 10.8 sec. Thus for the four wash cycles each including the stations 42 of S. W. and M for the time indicated at each station of a sequential heterogeneous assay, the time required is 30×10.8 or 324 seconds. Simultaneous assays use the four wash cycles consecutively. Sequential assays use the first wash cycle, then transfer off for incubation, then transfer back for the second, third, and fourth wash cycles.

Because of the sensitivity requirements of modern heterogeneous assays, it is very important that washing be done in a manner that produces very high efficiency as well as minimizing carry-over between vessels. The present invention produces near-zero background levels. This is done by performing two fairly "gross" washes by station W1 at steps 6 and 13. This is followed by a third wash in station W2, and a final fourth wash in station W2 to reduce the final background level to a lower value. As the term is used herein, "magnetic particles" or simply "particles responsive to a magnetic field" may be any of those known in the art. They are preferably ferromagnetic and have a small residual magnetism so that little clumping occurs in the absence of a magnetic field. Preferably magnetic particles of the type described by Lau et al. in U.S. Pat. No. 4,661,408, are employed. The separation stations S thereby separate the bound and free phases in order for the mixing process to proceed.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A method for performing immunoassays on concentrically mounted processing and incubating carousels, the incubating carousel having a predetermined number of reaction vessel support positions, the method comprising the steps of:

(a) adding reagents including a solid support to a sample in a reaction vessel on the incubating carousel;

(b) transferring the reaction vessel from the incubating carousel to a reaction vessel support position on the processing carousel using a transfer station which accesses both carousels;

(c) separating the solid support from the sample and reagents using processing stations disposed proximate said processing carousel; and, (d) washing the solid support using processing stations disposed proximate said processing carousel, wherein steps (c) and (d) comprise:

(e) advancing the processing carousel a first number of index positions and stopping at a processing station for a constant amount of time;

(f) advancing said processing carousel a second number of index positions and stopping at a processing station for said same constant amount of time;

(g) repeating steps (e) and (f) as necessary to complete a pre-processing operation in the instance of an immunoassay not requiring additional reagents; and, (h) in the instance of an assay requiring additional reagents, transferring a reaction vessel from the processing carousel to the incubating carousel at the first stopping of the reaction vessel at said transfer station and adding required reagents therein; and, (i) replacing the reaction vessel on said processing carousel before the pre-processing operation is completed, so that assays requiring an additional reagents may be processed on the processing carousel without changing the advancing motion of steps (e) and (f); and, (j) repeating steps (e) and (f) as necessary, so that sample processing times of the immunoassays not requiring additional reagents are not reduced.

2. The method of claim 1 wherein the total number of processing stations is selected so that each reaction vessel stops at every processing station and said transfer station exactly two times.

3. The method set forth in claim 1 wherein step (h) of transferring a reaction vessel from the processing carousel to the incubating carousel further includes the step of incubating the sample.

4. The method of claim 1 wherein each reaction vessel also stops at a dummy station exactly two times before the pre-processing of said samples is completed.

5. The method set forth in claim 4 wherein said predetermined number of reaction vessel support positions is fifteen.

6. The method set forth in claim 5 wherein said first number of index positions is six.

7. The method set forth in claim 5 wherein said second number of index positions is seven.

8. The method of claim 1 wherein advancing the processing carousel in steps (f) and (g) is in a single direction.

* * * * *